(12) United States Patent
Gritsenko

(10) Patent No.: US 7,239,901 B2
(45) Date of Patent: Jul. 3, 2007

(54) TISSUE SPECTROMETER WITH IMPROVED OPTICAL SHUTTER

(75) Inventor: Sergey I. Gritsenko, Hutchinson, MN (US)

(73) Assignee: Hutchinson Technology Incorporated, Hutchinson, MN (US)

( * ) Notice: Subject to any disclaimer, the term of this patent is extended or adjusted under 35 U.S.C. 154(b) by 766 days.

(21) Appl. No.: 10/440,947

(22) Filed: May 19, 2003

(65) Prior Publication Data

US 2004/0236198 A1 Nov. 25, 2004

(51) Int. Cl.
*A61B 5/00* (2006.01)
(52) U.S. Cl. ............... 600/310; 600/473; 600/476
(58) Field of Classification Search ......... 600/310, 600/316, 322, 323, 331, 473, 476
See application file for complete search history.

(56) References Cited

U.S. PATENT DOCUMENTS

| | | | | |
|---|---|---|---|---|
| 3,709,118 A | * | 1/1973 | Shoupp et al. | 396/185 |
| 4,176,958 A | | 12/1979 | Way et al. | |
| 4,348,092 A | * | 9/1982 | Hirohata et al. | 396/449 |
| 5,040,889 A | | 8/1991 | Keane | |
| 5,178,142 A | * | 1/1993 | Harjunmaa et al. | 600/310 |
| 5,379,764 A | * | 1/1995 | Barnes et al. | 600/473 |
| 5,460,182 A | * | 10/1995 | Goodman et al. | 600/473 |
| 5,596,992 A | * | 1/1997 | Haaland et al. | 600/473 |
| 5,830,134 A | * | 11/1998 | Caputo et al. | 600/322 |
| 5,879,294 A | | 3/1999 | Anderson et al. | |
| 6,097,975 A | * | 8/2000 | Petrovsky et al. | 600/322 |
| 6,377,840 B1 | | 4/2002 | Gritsenko et al. | |

FOREIGN PATENT DOCUMENTS

CA 999755 11/1976
EP 0 290 279 A1 9/1988

* cited by examiner

*Primary Examiner*—Eric F. Winakur
(74) *Attorney, Agent, or Firm*—Faegre & Benson LLP

(57) ABSTRACT

An improved system and method for calibrating spectrophotometric instruments for the effects of light source drift. An instrument includes both received light and reference light paths to a light sensor where light signals are converted to electrical signals to be used by a processor. A shutter is used to block or allow passage of one of the light signals to the sensor. When the selected light signal is blocked, the sensor produces an electrical signal representative only of the other signal. When the selected light signal is allowed to pass, the sensor produces an electrical signal representative of both light signals. By knowing the value of one of the signals by itself, the value of the other signal can be determined. The individual values are then processed to produce an output signal that is a function of both light signals. Further, because only one light path must be blocked, simpler structures for blocking the light may be used.

26 Claims, 10 Drawing Sheets

TISSUE SPECTROMETER WITH IMPROVED OPTICAL SHUTTER

FIELD OF THE INVENTION

The present invention relates generally to spectrophotometric instruments. In particular, the invention is an optical configuration and measurement signal acquisition and processing system for enhancing the output signal stability of a spectrophotometric instrument.

BACKGROUND OF THE INVENTION

Spectrophotometric-type instruments are known and used in a variety of applications. An instrument of this type is, for example, disclosed in the Anderson et al. U.S. Pat. No. 5,879,294. There remains, however, a continuing need for instruments capable of providing measurement to a higher degree of accuracy with relatively low levels of output signal drift.

An improvement to the spectrophotometric type instrument was the invention of U.S. Pat. No. 6,377,840 (Gritsenko et al.) wherein a reference light measurement was used improve the output signal. Prior art FIG. 1 shows a block diagram of wherein an instrument 10 includes an optical probe 12 which is releasably connected to an electronics package 14 via optical fibers 16. The electronics package 14 includes a connector 18, a detector 20, a processor/controller 22, and a display 24. In operation, the probe 12 is positioned on the tissue to be measured or analyzed. The probe 12 is interfaced to the instrument electronics through the optical fibers 16 and a probe connector 26. The probe connector 26 includes light emitting diodes (LEDs) or other light sources 30, 32, 34, 36, and 38 for generating light at a number of different wavelengths (e.g., 800, 760, 720, 680, and 530 nm, respectively). The light used to measure the characteristics of the tissue is coupled to the probe by send optical fibers 40, 42, 44, and 46. After being transmitted from the tissue-engaging surface of the probe 12 into the tissue being measured, the light will travel through the tissue before being collected at the end of the receive optical fiber 48. This collected light (measurement light signal) is then transmitted to the instrument 14 through the probe connector 26 and electronics package connector 18. A reference light signal corresponding to each of the measurement light signals (i.e., the reference light signals are not transmitted through the tissue) is also transmitted to the electronics package connector 18.

The collected measurement light signals and reference light signals received by the electronics package 14 are transmitted to the detector 20 which produces electrical signals representative of these light signals at each wavelength of interest. The processor/controller 22 then processes these signals to generate data representative of the measured tissue parameter (e.g., saturated oxygen level ($StO_2$)). The measurement reading can be visually displayed on the display 24. Algorithms used to compute the tissue parameter data are generally known and described in the Anderson et al. U.S. Pat. No. 5,879,294.

Calibration procedures are typically performed to enhance the accuracy of the measurements subsequently made by the instrument 14. Methods and devices for calibrating spectrophotometric-type instruments are generally known and disclosed in the Anderson et al. patent. The calibration can, for example, be performed by placing the probe 12 on a calibration device 50 such as that shown in prior art FIG. 1. The calibration device 50 includes a housing, which is filled with light scattering material. The light scattering material is generally spectrally flat (i.e., reflects all light to the same degree) to provide a reference spectrum. White polyethylene foam such as Plastazote LD45 available from Zotefoams plc. can be used for this purpose.

One configuration of a spectrophotometric instrument of the type described above includes, for each wavelength of interest, a photomultiplier tube (PMT) for detecting the measurement light signal, and a photodiode for detecting the calibration recognition signal (or ambient light). Thermal electric coolers can be included in the electronics package to help maintain temperature control of the optical bench to which the PMTs and photodiodes are mounted, and thereby reduce output signal drift.

The present invention is an optical bench configuration, measurement and reference signal acquisition system and measurement and reference signal processing algorithm which provide relatively low levels of output signal drift. The probe connector 26 used in connection with this invention is illustrated in prior art FIG. 2, which shows an embodiment having a reference signal generated within the connector. As shown, the probe connector 26 includes 4 LEDs 30, 32, 34, and 36 for generating the measurement light signals at 800, 760, 720 and 680 nm. Light signals from each of these LEDs are coupled to the probe 12 by a separate measurement signal send fiber 40, 42, 44, 46. After being transmitted through the tissue being analyzed and collected at the probe, the measurement light signal is coupled back to the probe connector by a measurement signal receive fiber 16C. The end of the measurement signal receive fiber 16C terminates in the probe connector 26 at a sample ferrule 52 which is adapted to mate with a socket in the connector 18 of the electronics package 14.

The probe connector 26 also provides a reference light signal. The reference light signal includes a portion of the light from each of the LEDs, and has not been transmitted from the probe before being collected. In the embodiment shown in prior art FIG. 2, the reference light signal is collected by reference light signal send optical fibers 54, 56, 58, and 60 which extend respectively from each measurement light signal source LED 30, 32, 34, 36. The reference light received from each LED is mixed using a mixer 62 and transmitted through the reference signal fiber 16B. The end of the reference signal fiber 16B terminates in the probe connector 26. Since it is significantly attenuated when it is transmitted through the tissue, the intensity of the measurement light signal at the connector is much less than the intensity of the non-attenuated reference light signal (e.g., about 1 million times less). In order to match the reference and measurement signal magnitudes to enable detection with a similar photo multiplier tube gain, the reference signal is attenuated at the mixer 62. The reference signal attenuation is obtained by reflectance mode positioning the reference signal send fibers 54, 56, 58, 60 equidistant from the centrally located reference signal receive fiber 16B. The concentration of scattering material (such as titanium dioxide from Aldrich, Milwaukee, Wis.) within an optically clear epoxy substrate (such as EpoTech 301 from Epoxy Technology, Billerica, Mass.) can be adjusted to provide the appropriate level of attenuation within the mixer 62.

Light transmitted from the probe tip 12 from send fiber 16A is collected through the probe tip by receive fiber 16C which may also be connected to the monitor by probe connector 26.

In the monitor, a tissue value represented by the reflected light intensity and wavelength distribution can be determined. The received light signal is directed to the detector or optical bench 20 for separation into selected component wavelengths that are then passed to a processor 22 for processing. Similarly, the reference light signal is directed to the optical bench for separation into its component wavelengths. The reference light signal is used to correct the value of the received light signal.

The same optical bench is used for measuring both sample and reference signals to compensate for the drift. Accordingly, a shutter system 80 was used to alternately permit or prohibit one of light signals from reaching the optical bench when the other light signal is being analyzed. The prior art shutter system 80 included motor 87, and shutter 84. The shutter 84 was shaped so that when one light transmission path was blocked, the other path could transmit light through aperture plate 86. Motor 87 positioned the shutter to prevent passage of light by one of the two light signals.

SUMMARY OF THE INVENTION

The present invention is a simplified reference light measurement system for use in spectrometers. A shutter is placed in the path of only one of the light signals being fed back to the sensors, preferably the reference light signal. When the light source is off and with the shutter in any position, the sensors produce a signal reflective of a dark source. With the light source on and the shutter closed (blocking the reference light signal), the sensors will produce a signal reflective of the dark source plus the light gathered from the tissue under test. Finally, with the light source on and the shutter opened, the sensors will produce a signal reflective of the dark source plus the light gathered from the tissue plus the light from the reference fiber. By knowing the dark signal value, the dark signal and tissue return signals together and then the dark signal plus the tissue return signal plus the reference signal, each of the individual signals can be determined (three signals and three unknowns). There is no need to alternate between just the reference signal and just the return signal in order to calculate the desired end value.

Further, such a method may be implemented using a flat coil and a shutter carrying a magnet. By appropriate placement of the coil relative to the shutter carrying the magnet, the energization/de-energization of the coil causes movement of the shutter into and out of the light signal path. Because the flat coil and flexible shutter are relatively small, this allows the probe of the spectrophotometric instrument to carry the shutter system. Lastly, the coil and flexible shutter and flat coil are of significantly lower cost than the shutter systems of the prior art.

DETAILED DESCRIPTION OF THE PREFERRED EMBODIMENTS

Figure 1:
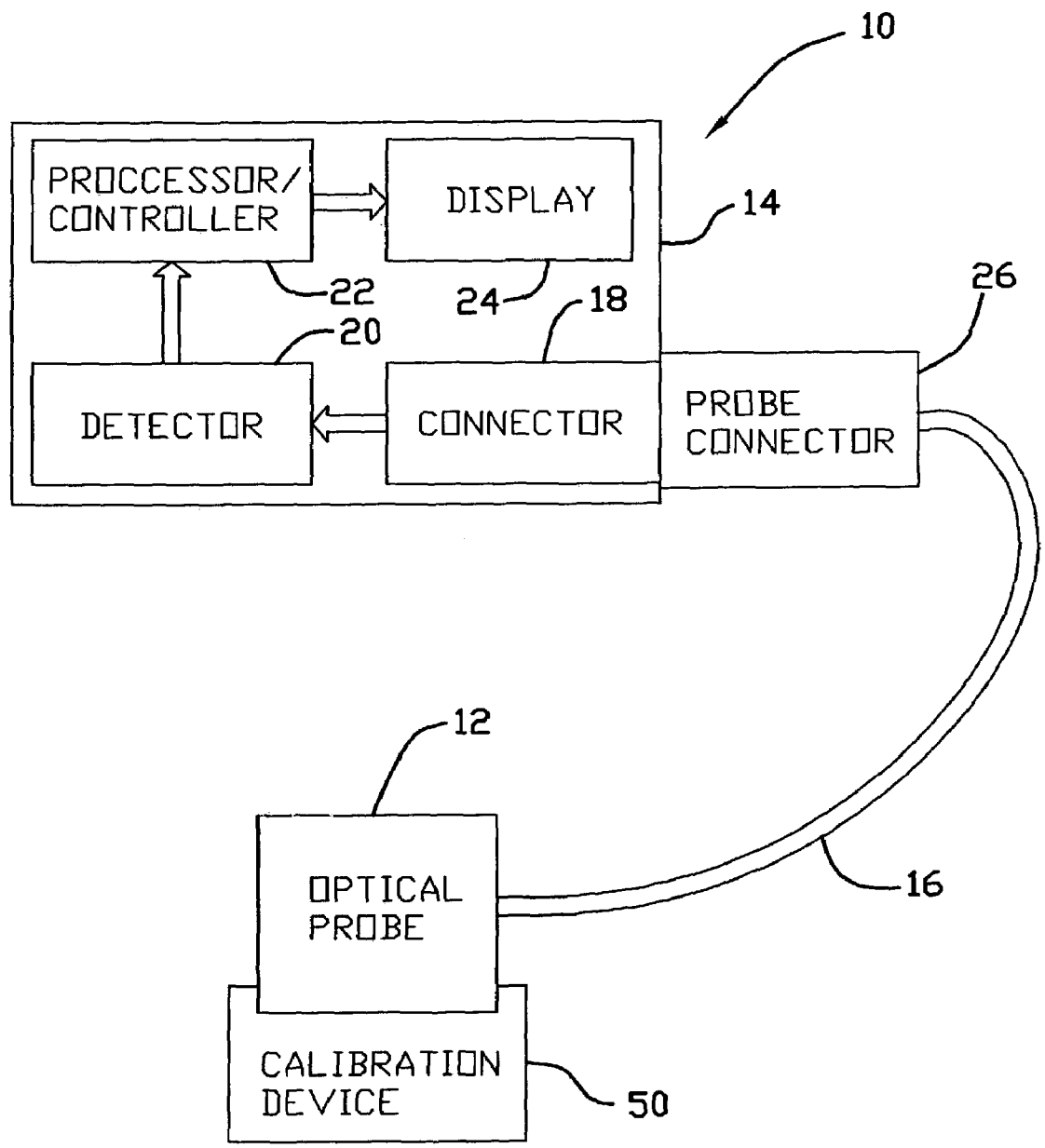
FIG. 1 is block diagram of a prior art instrument along with a probe connector and optical probe connected by optical fibers and a calibration device.
Figure 2:
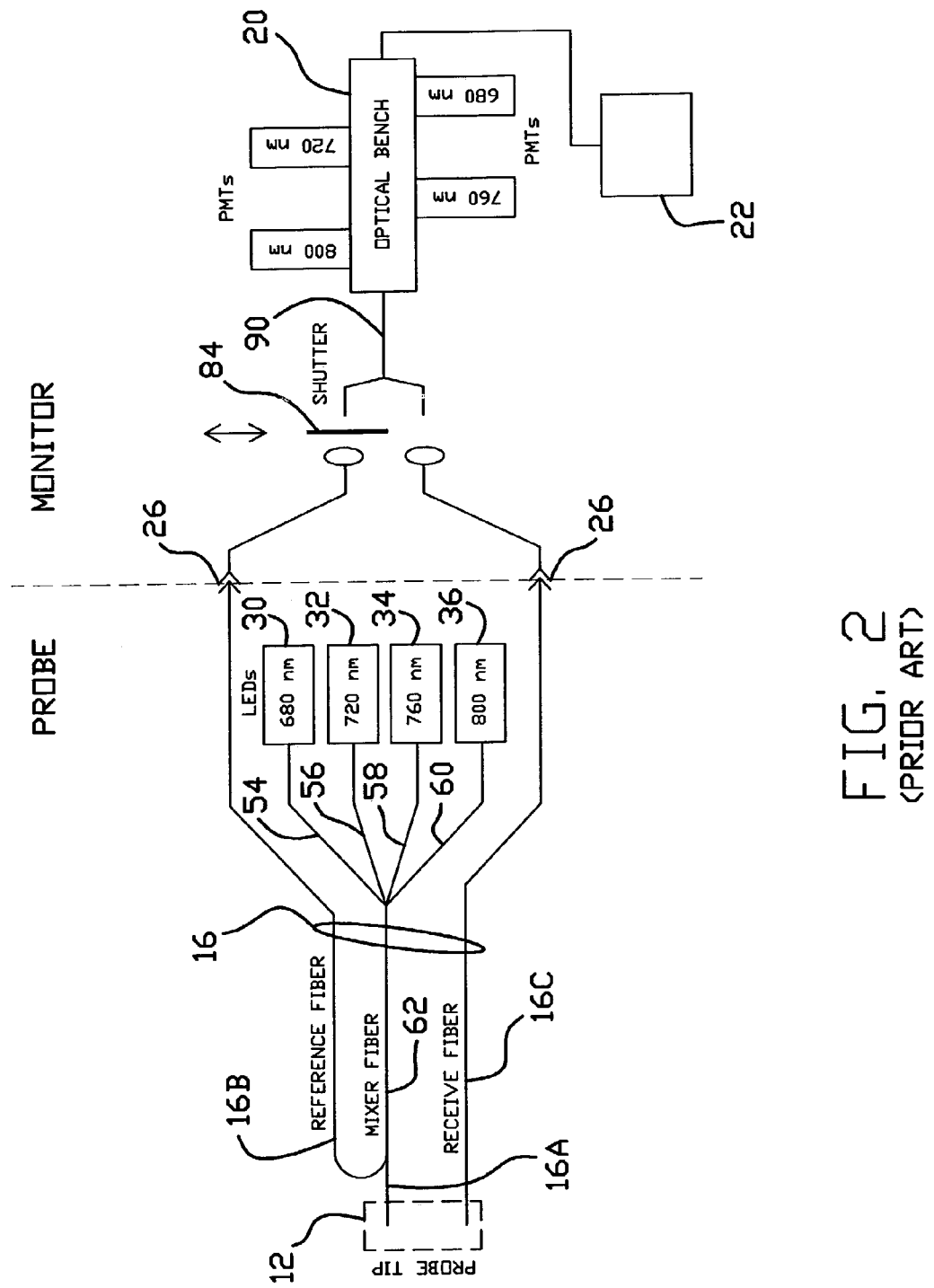
FIG. 2 is a detailed view of the prior art probe connector shown in FIG. 1.
Figure 3:
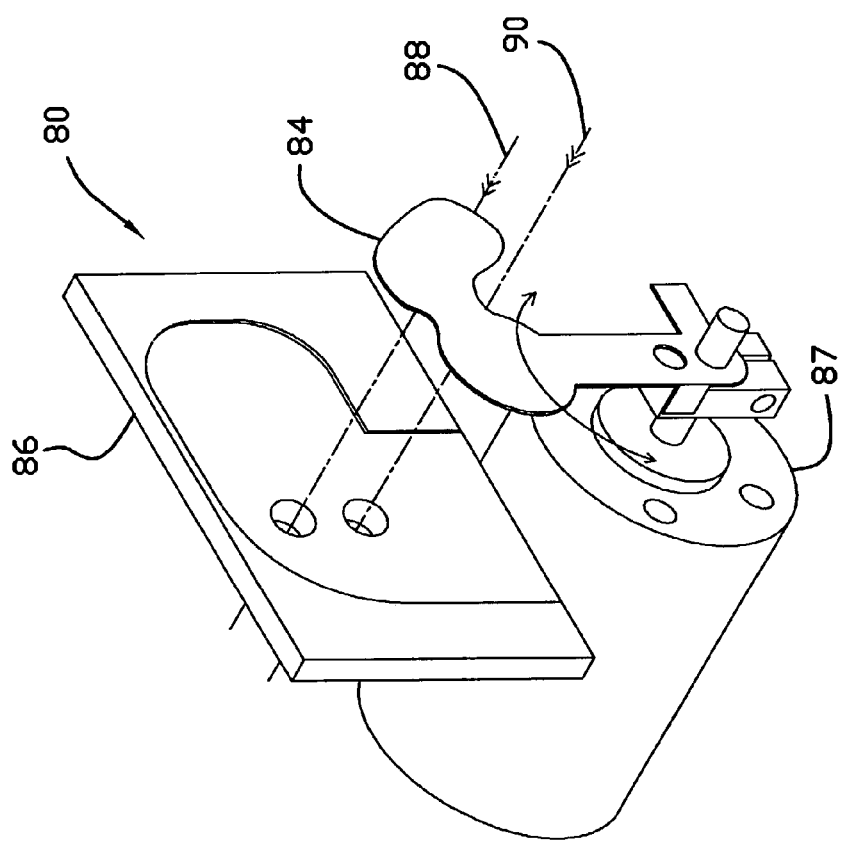
FIG. 3 is a block diagram of the prior art reference light system and method.
Figure 4:
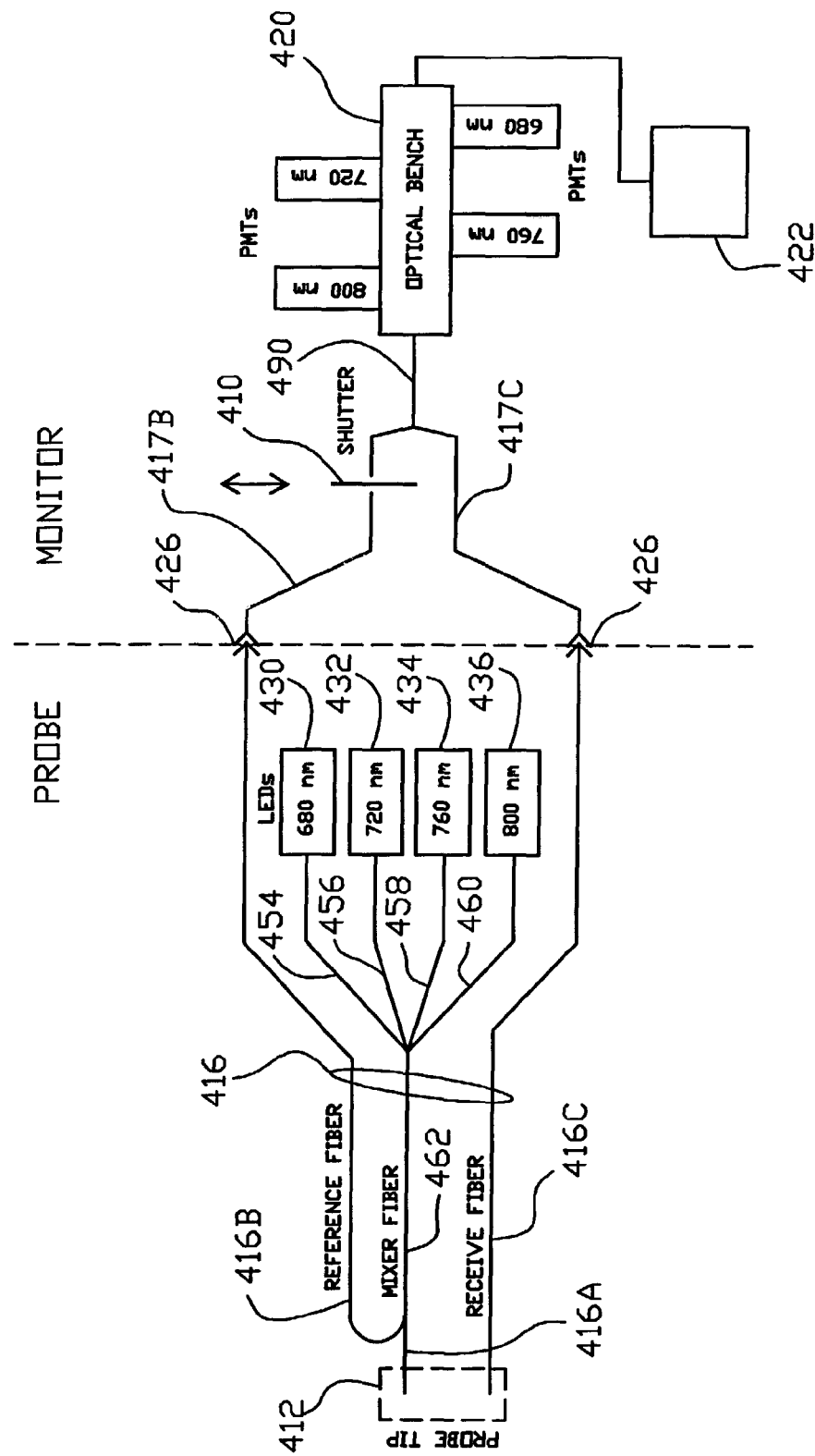
FIG. 4 is a block diagram of a first embodiment of the presently inventive reference light system and method.

Referring now to FIG. 4 there shown is a block diagram of the presently inventive spectrophotometric instrument system 400. Like reference numbers in FIG. 4 represent the same elements as in FIG. 2. The system includes a monitor portion and a probe portion. The probe portion includes light emitting diodes (LEDs) 430, 432, 434 and 436, light fibers 454, 456, 458 and 460, mixer fiber 462, send fiber 416A, receive fiber 416C, reference fiber 416B and optical bench fiber 490. Light signals from the LEDs are transmitted to the mixer fiber 462 where the light signals are mixed. Reference fiber 416B is used to convey a reference light signal to the monitor for use in calibrating the unit to produce a more accurate output signal. Send fiber 416A carries a mixed light signal (which is the same as the reference light signal) to the probe tip 412 for transmission into the target (e.g. a patient undergoing tests). Receive fiber 416C collects light from the target that was introduced into the target by the send fiber.

The reference fiber and the receive fiber are coupled to the monitor through connector or connectors 426. The number of connectors used is not essential to the invention.

The monitor side of the device includes a Shutter 410, monitor reference fiber 417B, monitor receive fiber 417C, optical bench 420 and processor 422. Shutter 410 is used to alternately interrupt and allow passage of the reference light signal to the optical bench. The received light signal passes through the monitor receive fiber 417C without interruption by the shutter. Shutter as used in this application could mean a mechanical shutter, an optical filter or injection of a counter light signal.

Optical Bench fiber 490 then carries the received light signal and the reference light signal (when it gets past the barrier) to the optical bench 420. The optical bench 420 may be made from, for example, photo-multiplier tubes that generate a signal that is a function of the presence of light at a predetermined wavelength. These signals are then passed to the processor 422 for determination of a final output signal. Such a process may occur as is described in U.S. Pat. No. 5,879,294 (Anderson et al.) which is incorporated herein by reference.

One important feature of the invention is that only the reference light signal is subject to interruption at the optical bench. By eliminating the shutter from the received light signal path to the optical bench, many timing issues are eliminated (from both processing and movement of the shutter). Further, the shutter may be substantially simplified and even relocated.

Eliminating the shutter from the received light signal causes a change in how the processor handles the signals from the optical bench. When the LEDs are off and with the shutter in any position, the optical bench produces a signal reflective of a dark source (here called the dark signal). With the LEDs on and the shutter closed (blocking the reference light signal), the sensors will produce a signal reflective of the dark source plus the light gathered from the tissue under test. Finally, with the LEDs on and the shutter opened, the sensors will produce a signal reflective of the dark source plus the light gathered from the tissue plus the light from the reference fiber. This provides three equations and three unknowns:

LEDs Off, Shutter in any position=dark signal (1)

LEDs On, Shutter–Blocking=dark signal+received signal (2)

LEDs On, Shutter–Not Blocking=dark signal+received signal+reference signal (3)

By knowing the dark signal value first (equation 1) and then the dark signal plus the received signals together (equation 2), the value of the received signal can be determined by subtracting the dark signal value from the signal of equation 2. Then by knowing the dark signal and the received signal individually, the reference signal can be determined from equation 3. There is no need to alternate between just the reference signal and just the return signal in order to calculate the desired end value.

In the alternative, the shutter could be used to block only the received signal path (not shown). The equations would then be LEDs Off, Shutter in any position=dark signal (4)

LEDs On, Shutter–Blocking=dark signal+reference signal (5)

LEDs On, Shutter–Not Blocking=dark signal+reference signal+received signal (6)

The three equations and three unknowns can then be solved in a manner similar to the one described above.

Figure 5:
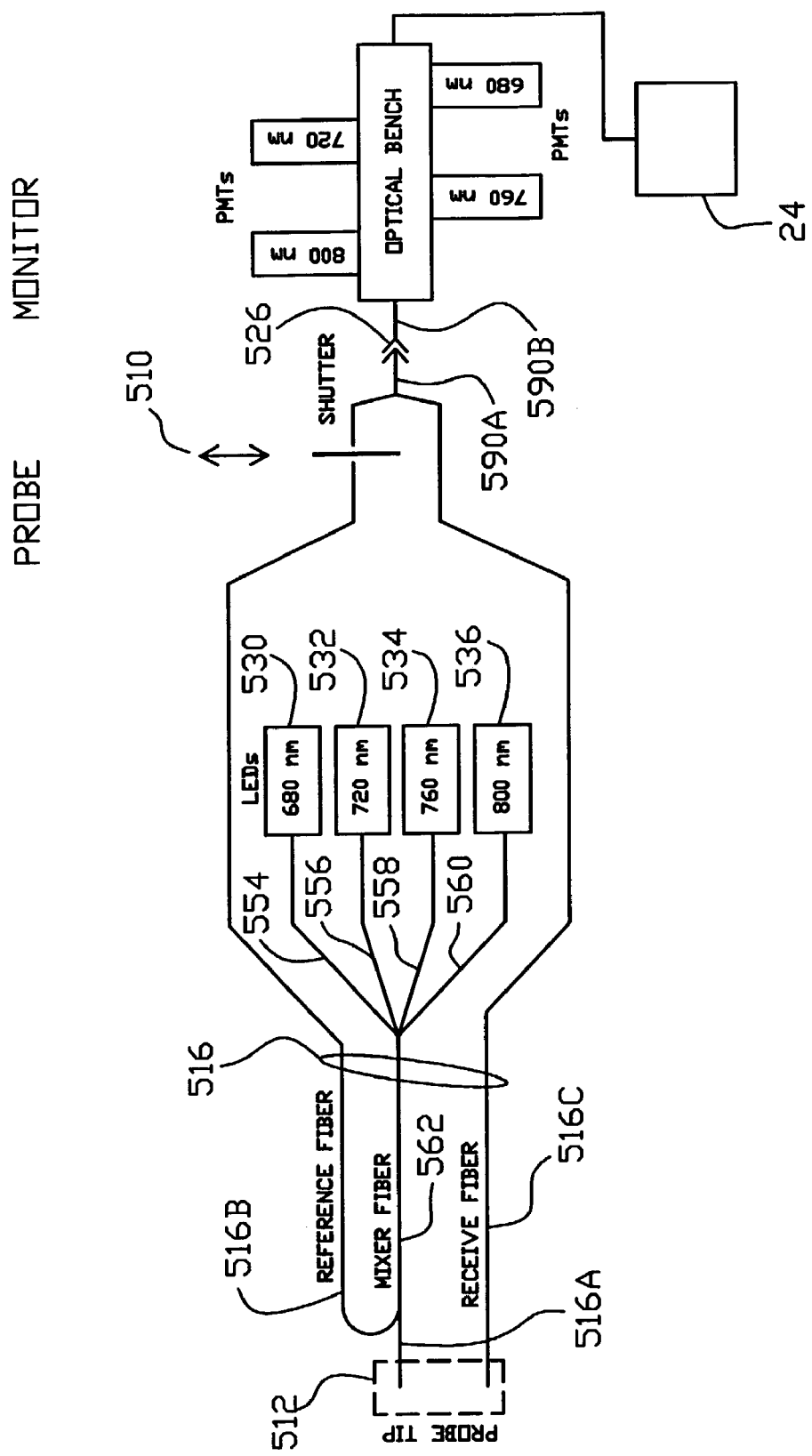
FIG. 5 is a block diagram of a second embodiment of the presently inventive reference light system and method.
Figure 6:
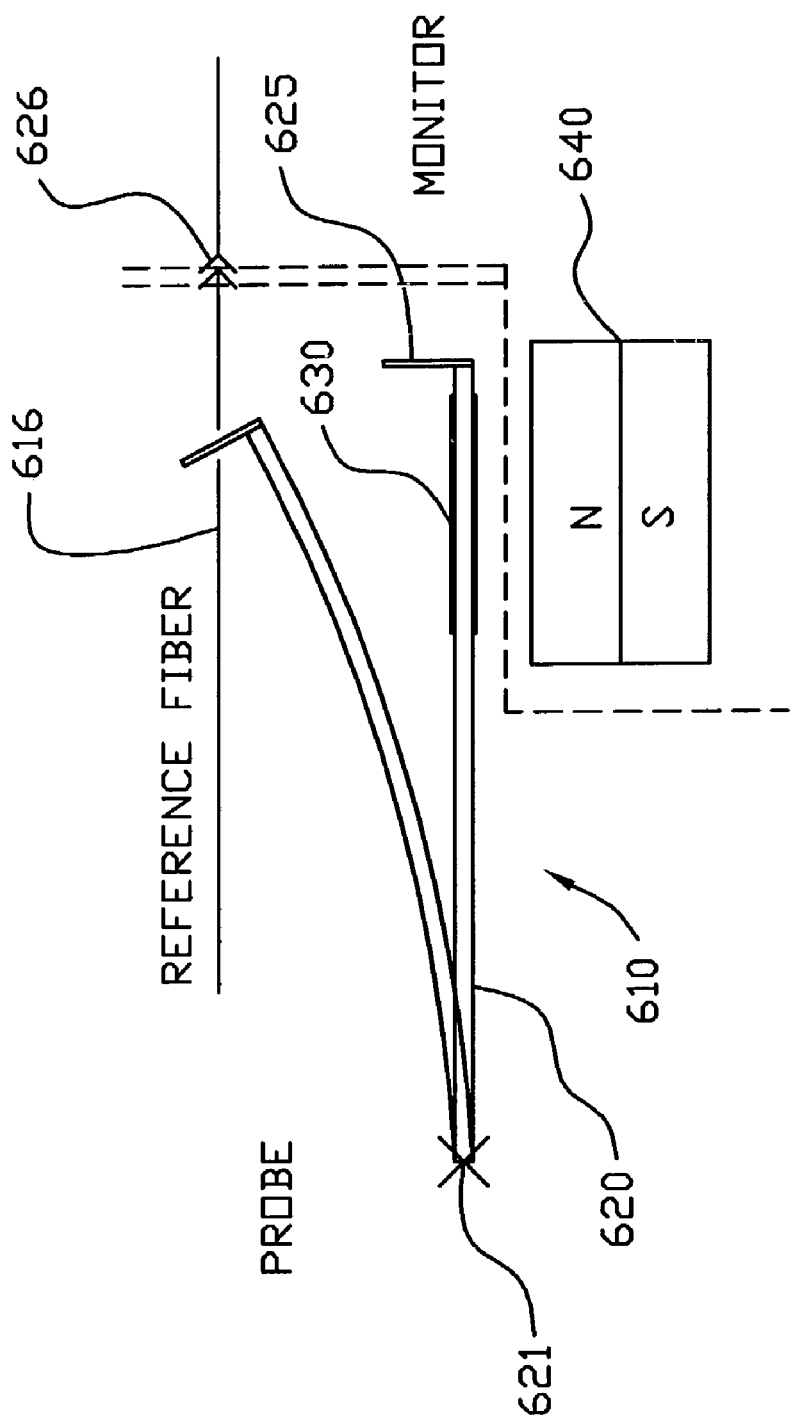
FIG. 6 is a plan view of a shutter implemented according to the present invention.

Referring now to FIG. 5, there shown is an alternative embodiment of the present invention where like numbers represent the same components from FIG. 4. Note however that there is only one connector 526 shown and that the connector splits the optical bench fiber into two pieces 590A and 590B. This is due to placement of the shutter 510 in the probe instead of the monitor portion of the device. One structure well suited for implementing the shutter in the probe portion of the device is shown in FIG. 6. FIG. 6 shows a shutter 610 that includes beam 620, obstruction 625, flat coil 630 and magnet 640. Beam 620 is fixed in place at end 621 and is preferably made of a thin, relatively flexible material such as flexible printed circuit board. While a flexible printed circuit board is preferred, any relatively flat flexible isolator capable of holding conductive paths will work. Obstruction 625 is preferably placed in an end region opposite fixed end 621 and is free to move radially around the fixed end.

Flat coil 630 and magnet 640 cooperate to cause deflection and return of beam 620. The flat coil is shown in more detail in FIG. 7. When an electric current passes through the flat coil, a magnetic field is produce that is directed along an axis perpendicular to the center of the coil. Depending upon the orientation of the north and south poles of the magnet, this will cause deflection of the beam either towards or away from the magnet. In essence, the shutter has become a micro-solenoid. As can be seen from FIG. 6, when the beam is deflected away from the magnet, the obstruction directed to a gap in the reference fiber.

Figure 7:
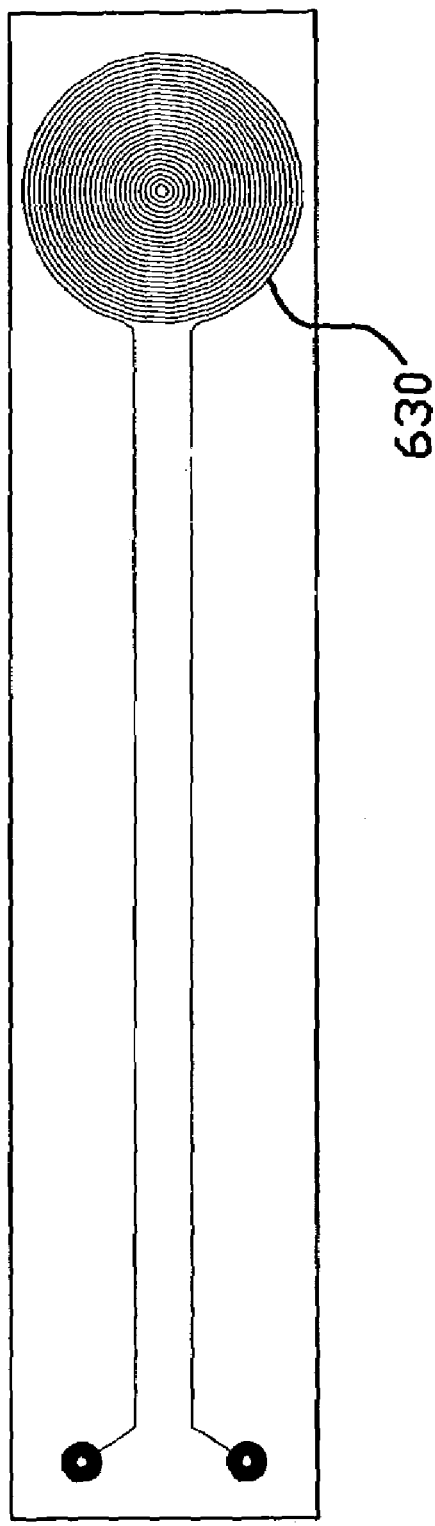
FIG. 7 is a plan view of a flat coil used in the present invention.

The flat coil may be manufactured using a flexible circuit substrate. A conductive path in the shape of coil (as shown in FIG. 7) is then laid out on both sides of the circuit board in any manner as is well known in the art. Alternatively, the coil can be on one side of the substrate with a conductive path on the other sides to make a connection to the center of the coil. In another alternative, the coil can be made using multi-layer technology, with any even number of layers. In one embodiment, the flat coil is located in the vicinity of the connector (426, 526, 626). The magnet is positioned in close proximity on the monitor. While the magnet may be relatively expensive, the flat coil may be relatively inexpensive. This means that the entire probe assembly may be made to be disposable.

Figure 10:
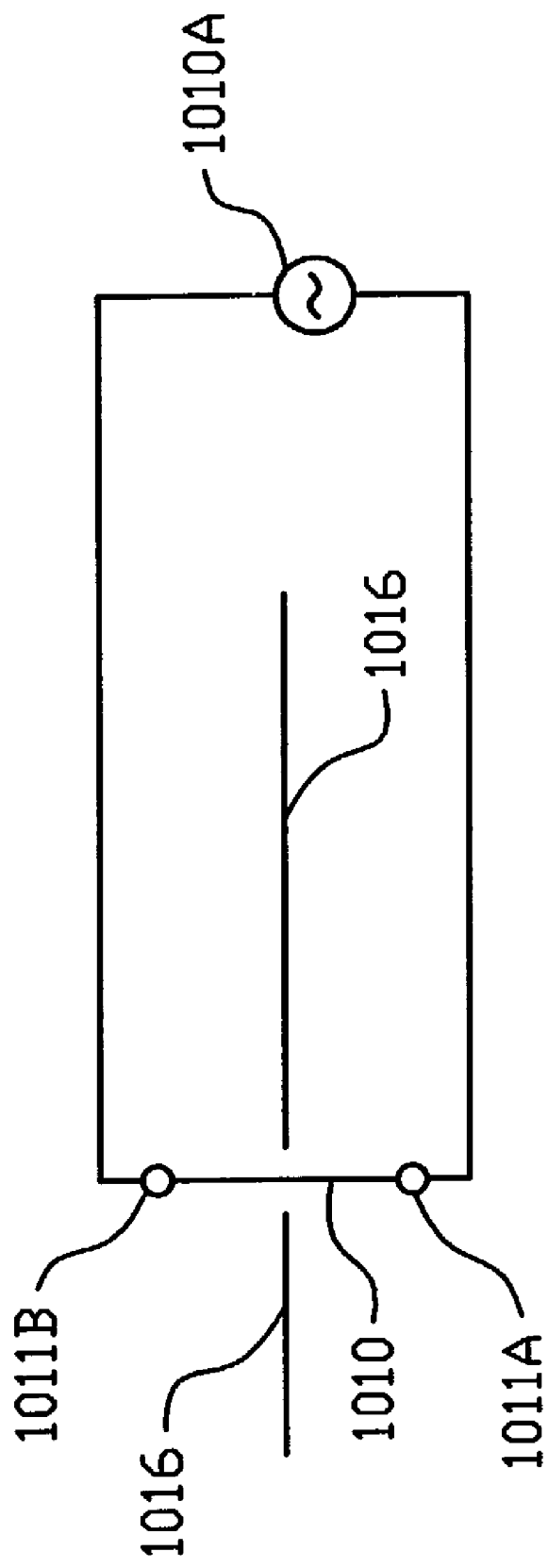
FIG. 10 is a block diagram of an alternate embodiment of the present invention.

Referring now to FIG. 10, there shown is an alternative shutter arrangement. Shutter 1010 is an electro-optical shutter. In one embodiment, the optical shutter is based on ferroelectric liquid crystal technology, which either allows or stops light from passing therethrough based upon the electrical voltage placed at its terminals 1011A and B. Driver 1010A may produce a signal similar to that shown in FIG. 8 in order to producing a desired time relationship for passage of the reference light signal through fiber 1016. A suitable optical shutter is one of the LV (1300-AC, 2500-AC, 1300P-OEM, 2500P-OEM, 4500P-OEM, 2525P-SQ, 3325P-OEM) line of products from Displaytech, 2602 Clover Basin Drive, Longmont, Colo. 80503. The driver 1010A may be a Displaytech DR50 driver.

Figure 8:
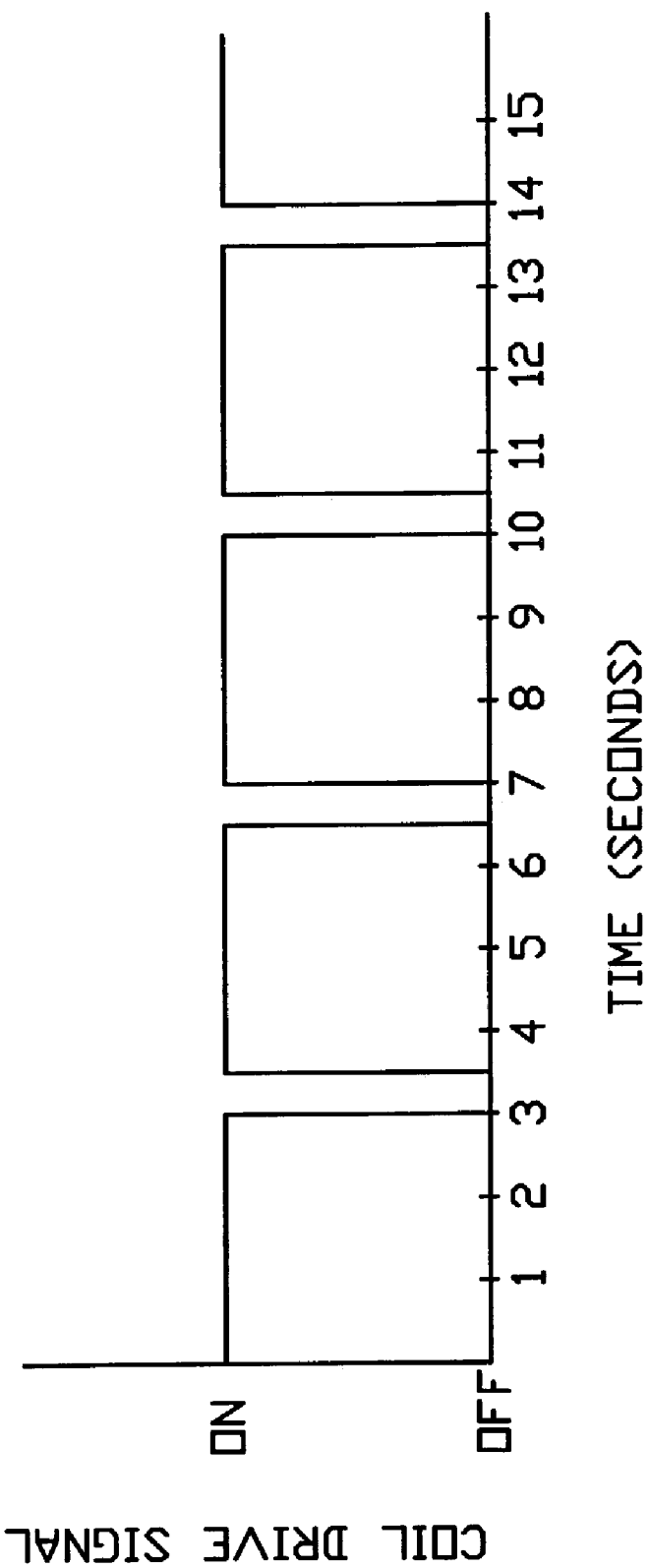
FIG. 8 timing diagram showing the on-off cycling of the coil drive of the present invention.

Referring now to FIG. 8, there shown is a timing signal for driving the coil 630 as per one embodiment. In this embodiment, the coil signal is on for three seconds and off for one-half of a second. This, again in one embodiment, produces a return signal plus the dark signal for the three second period without including the reference light. Then, when the drive signal is off, the reference signal is included in the signal presented to the optical bench.

Figure 9:
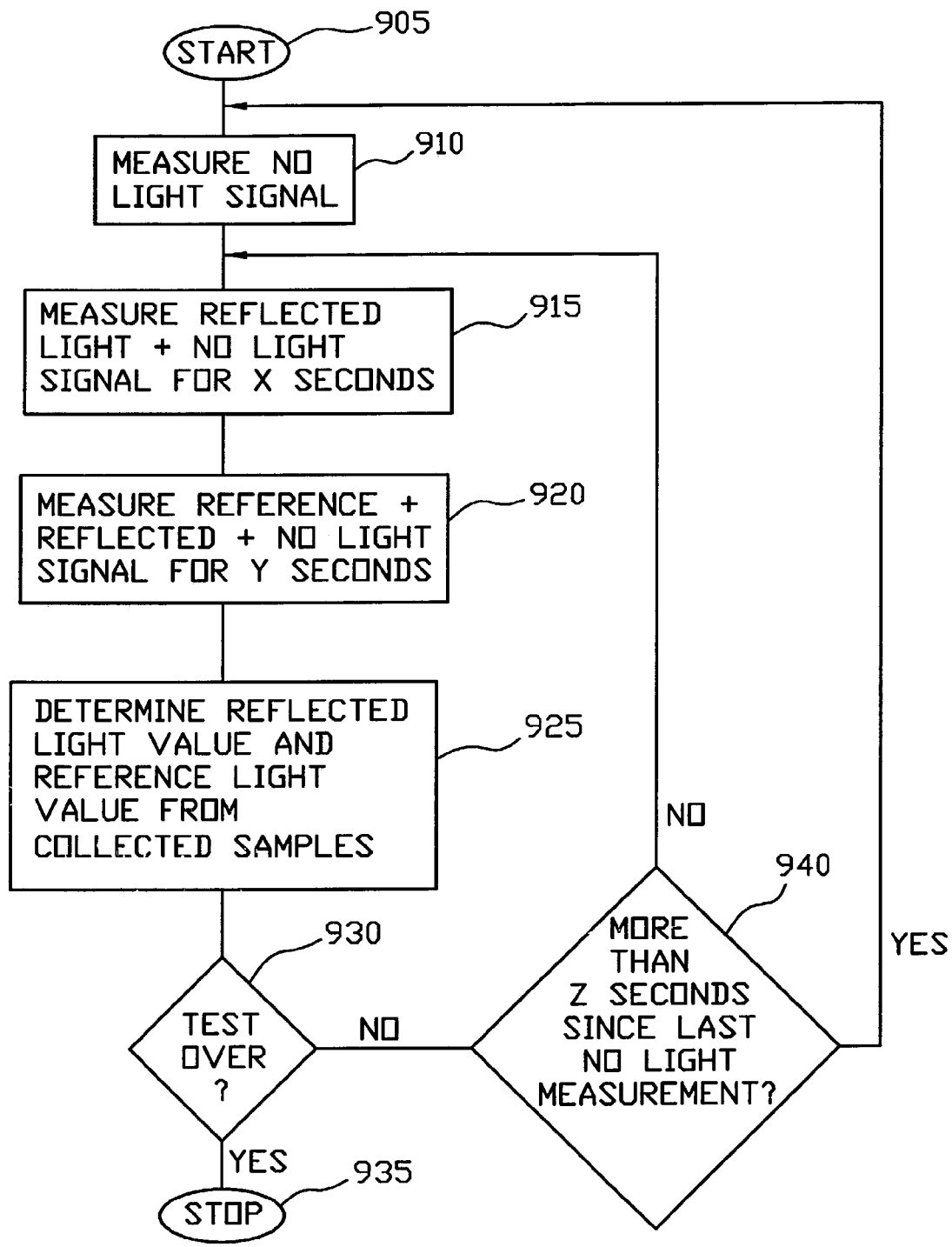
FIG. 9 is a flow chart of the presently inventive method.

FIG. 9 is a flow chart of the method used to determine the value of the reflected signal when a reference signal is used to determine attributes of the light source(s). After starting at block 905, the system measures a no light signal (signal received by the optical bench when the light source(s) are off) at block 910.

Then, at block 915, the light source is turned on and a value is determined for the signal at the optical bench that has components of light reflected from the patient plus the no light signal. At this point, the shutter is positioned to prevent the reference light from reaching the optical bench. Such a measurement is taken for a predetermined amount of time, preferably corresponding to the coil drive signal. In one embodiment, the time is 3.5 seconds.

Next, at block 920, the reference light is allowed to reach the optical bench along with the reflected light. Thus, the optical bench produces a light signal having components of the no light signal, the reference light and the reflected light. This combination of signals reaches the optical bench for a second predetermined amount of time Y. In one embodiment, Y is one-half of a second.

Once the necessary signals have been collected, a unique value can be determined for the reference signal and the reflected signal and the reflected signal can be corrected using the reference signal. The method of determining the signal values is described with respect to equations 1–3 above.

Alternatively, the optical shutter could interrupt the reflected signal path to the optical bench. In this case, equations 4–6 would be used.

The invention is not to be taken as limited to all of the details thereof as modifications and variations thereof may be made without departing from the spirit or scope of the invention.

What is claimed is:

1. A spectrophotometric instrument; comprising:
a source of measurement light signals having measurement light wavelengths;
a probe having:
 a tissue-engaging surface;
 a send fiber coupled to the measurement light signal source for transmitting the measurement light signals to the tissue-engaging surface; and
 a receive fiber for receiving light including the measurement light signals after the measurement light has been transmitted through the tissue;
reference signal optics coupled to the measurement light signal between the measurement light signal source and the tissue-engaging surface, for transmitting a reference light signal portion of the measurement light signal;
a detector for generating electrical signals representative of the measurement light signals and the reference light signals;
an optical path for coupling the measurement light signal from the receive fibers and the reference light signal portion from the reference signal optics to the detector;
an optical path control for selectively allowing and preventing the reference light signal portion to the detector, whereby the detector can output a reference light sample value when the reference light signal portion is coupled to the detector, and the detector can output a measurement light sample value when the measurement light signal portion is coupled to the detector; and
a processor for determining corrected measurement sample signals at each measurement light wavelength as a function of a no light signal, a current measurement signal plus a no light signal and a no light signal plus a current measurement signal plus a current reference signal.

2. The instrument of claim 1, wherein the processor further determines the values of a no light signal, a measurement light signal and a reference light signal.

3. The instrument of claim 1 wherein the optical paths include optics.

4. The instrument of claim 3 wherein the optics include an attenuator in the reference light signal path for reducing the portion of the reference light signal that is directed to the detector.

5. The instrument of claim 1 wherein the path control includes a shutter.

6. The instrument of claim 5 and further including an electric drive for driving the shutter.

7. The instrument of claim 1 wherein the measurement light signal source includes a plurality of sources of narrow-bandwidth light.

8. The instrument of claim 1 wherein the reference signal optics includes an optical fiber.

9. The instrument of claim 1 wherein the reference signal optics further includes a light mixer.

10. A spectrophotometric instrument, including
a measurement signal optical input for receiving a measurement light signal transmitted through tissue being analyzed;
a reference signal optical input for receiving a reference light signal which is a portion of the measurement light signal that has not been transmitted through the tissue being analyzed;
a detector for generating electrical signals representative of the measurement light signals and the reference light signals;
optical paths for coupling the measurement light signal from the measurement signal optical input and for coupling the reference light signal from the reference signal optical input to the detector; and
an optical path control for selectively allowing and preventing only the reference light signal to the detector, the detector outputting a reference light sample value as a function of a no light signal, a current measurement signal and a reference light signal.

11. The instrument of claim 10 and further including a processor/controller for calculating corrected measurement values as a function of a combined current measurement light signal and reference light signal.

12. An optical sensor, comprising:
a light source;
a first optical path for directing light to a first location;
a second optical path for collecting light from a second location;
a detector connected to the second optical path for generating electrical signals representative of the light collected in the second optical path;
a third optical path for direction of light from the light source to the detector, wherein the third optical path bypasses the first and second locations; and
a shutter in the third optical path for selectively allowing and preventing light only in the third optical path from reaching the detector.

13. The optical sensor of claim 12, wherein the shutter comprises:
a flat coil having a coiled end and a free end with a vane mounted on the free end;
a power source operatively connected to the flat coil for energizing and de-energizing the flat coil; and
a magnet positioned near the free end of the flat coil whereby the flat coil is in a first position when energized and a second position when de-energized.

14. A spectrophotometric instrument; comprising:
a source of measurement light signals having measurement light wavelengths;
a probe having:
 a tissue-engaging surface;
 a send fiber coupled to the measurement light signal source for transmitting the measurement light signals to the tissue-engaging surface; and
 a receive fiber for receiving light including the measurement light signals after the measurement light has been transmitted through the tissue;
reference signal optics coupled to the measurement light signal between the measurement light signal source and the tissue-engaging surface, for transmitting a reference light signal portion of the measurement light signal;
a detector for generating electrical signals representative of the measurement light signals and the reference light signals;
a first optical path for coupling the measurement light signal from the receive fiber to the detector;
a second optical path for coupling the measurement light signal from the reference light signal portion from the reference signal optics to the detector; and
an optical path control only in the second optical path for selectively allowing and preventing the reference light signal portion to the detector, whereby the detector can output a reference light sample value when the reference light signal portion is coupled to the detector, and the detector can output a measurement light sample value when the measurement light signal portion is coupled to the detector.

15. The instrument of claim 14, further comprising:
a processor for determining the values of a no light signal, a measurement light signal and a reference light signal.

16. The instrument of claim 14 wherein the optical paths include optics.

17. The instrument of claim 16 wherein the optics include an attenuator in the reference light signal path for reducing the portion of the reference light signal that is directed to the detector.

18. The instrument of claim 14 wherein the path control includes a shutter.

19. The instrument of claim 18 and further including an electric drive for driving the shutter.

20. The instrument of claim 14 wherein the measurement light signal source includes a plurality of sources of narrow-bandwidth light.

21. The instrument of claim 14 wherein the reference signal optics includes an optical fiber.

22. The instrument of claim 14 wherein the reference signal optics further includes a light mixer.

23. The instrument of claim 14 and further including a processor/controller for calculating corrected measurement sample signals at each measurement light wavelength as a function of a no light signal, a current measurement signal plus a no light signal and a no light signal plus a current measurement signal plus a current reference signal.

24. A method of adjusting an output signal for light source drift in a instrument that uses a light signal to measure an attribute of a target, comprising the steps of:
directing a light signal from the light source at the target;
redirecting a portion of the light signal as a reference light signal to a sensor input terminal;
collecting a portion of the light signal from the target to create a received light signal and directing the received light signal to the sensor input terminal;
blocking only one of the light signals selected from the group of the reference light signal and the received light signal at pre-selected times so that the sensor produces a first signal for the non-selected light signal that does not contain a component of the selected light signal and a second signal that contains components of both light signals; and
making an output signal that is a function of the first and second signals.

25. The method of claim 24, wherein the blocking step further comprises the steps of:
selecting the reference light signal.

26. The method of claim 25, comprising the further steps of: determining the first signal value as a function of the received light signal.

* * * * *